(12) United States Patent
Muto et al.

(10) Patent No.: US 8,859,226 B2
(45) Date of Patent: Oct. 14, 2014

(54) MEASUREMENT METHOD FOR VIABLE CELL COUNT, AND CULTURE MEDIUM

(75) Inventors: Masamichi Muto, Zama (JP); Fumiaki Abe, Zama (JP); Tomoko Yaeshima, Zama (JP)

(73) Assignee: Morinaga Milk Industry Co., Ltd., Tokyo (JP)

( * ) Notice: Subject to any disclaimer, the term of this patent is extended or adjusted under 35 U.S.C. 154(b) by 0 days.

(21) Appl. No.: 13/390,859

(22) PCT Filed: Mar. 25, 2011

(86) PCT No.: PCT/JP2011/057337
§ 371 (c)(1),
(2), (4) Date: Feb. 16, 2012

(87) PCT Pub. No.: WO2011/118765
PCT Pub. Date: Sep. 29, 2011

(65) Prior Publication Data
US 2012/0149054 A1 Jun. 14, 2012

(30) Foreign Application Priority Data
Mar. 26, 2010 (JP) .................. 2010-072368

(51) Int. Cl.
*C12N 1/20* (2006.01)
*C12Q 1/06* (2006.01)
*C12Q 1/04* (2006.01)

(52) U.S. Cl.
CPC *C12Q 1/045* (2013.01); *C12Q 1/06* (2013.01); *G01N 2333/36* (2013.01); *C12N 1/20* (2013.01)
USPC .......................................................... 435/29

(58) Field of Classification Search
None
See application file for complete search history.

(56) References Cited

FOREIGN PATENT DOCUMENTS

| JP | 58224685 A | 12/1983 |
|---|---|---|
| WO | 03048343 A1 | 6/2003 |
| WO | 2009145306 A1 | 12/2009 |
| WO | 2009157316 A1 | 12/2009 |
| WO | WO2009157316 | * 12/2009 |

OTHER PUBLICATIONS

Mikkelsen et al. "Enumeration of Bifidobacteria in Gastrointestinal Samples from Piglets" Applied and Environmental Microbiology.*
Abe et al. "Safety evaluation of probiotic bifidobacteria by analysis of mucin degradation activity and translocation ability" Anaerobe 16(2010) 131-136. Available online Jul. 26, 2009.*
Sigma Aldrich, "69966 MRS Broth (*Lactobacillus* Broth acc. to De Man, Rogosa, and Sharpe)" Jul. 1, 2002., includes results showing date.*
Hadadji et al. "Identification of cultivable *Bifidobacterium* species isolated from breast-fed infants feces in West-Algeria" African Journal of Biotechnology vol. 4 (5), pp. 422-430, May 2005.*
Nebra et al. "A New Selective Medium for *Bifidobacterium* spp." Applied and Environmental Microbiology 1999, 65(11): 5173-5176.*
Simpson et al. "The evaluation of a mupirocin-based selective medium for the enumeration of bifidobacteria from probiotic animal feed" Journal of Microbiological Methods 57 (2004) 9-16.*
Mitsuoka et al., Research on bifidobacteria, Japan Bifidus Foundation, 1994, pp. 266-267.
Mitsuoka et al., Research on bifidobacteria, Japan Bifidus Foundation, 1994, pp. 282-283.
Anonymous, Enumeration method for *Bifidobacterium* within fermented milk and *Lactobacillus* beverages, *Bifidobacterium* Testing Methods Review Committee of the Japanese Association of Fermented Milks and Fermented Milk Drinks, 2000, pp. 1-13.
Sneath et al., Bergey's Manual of Systematic Bacteriology, 1986, pp. 1428-1431, vol. 2.
Pastell et al., In Vitro Fermentation of Arabinoxylan-Derived Carbohydrates by Bifidobacteria and Mixed Fecal Microbiota, Journal of Agricultural and Food Chemistry, 2009, pp. 8598-8606, vol. 57, No. 18.
Moura et al., In vitro fermentation of xylo-oligosaccharides from corn cobs autohydrolysis by *Bifidobacterium* and *Lactobacillus* strains, LWT, 2007, pp. 963-972, vol. 40.
Savard et al., Determination of Differentially Expressed Genes Involved in Arabinoxylan Degradation by *Bifidobacterium longum* NCC2705 Using Real-Time RT-PCR, Probiotics & Antimicro. Prot., 2009, pp. 121-129, vol. 1.
Roy et al., Evaluation of rapid methods for differentiation of *Bifidobacterium* species, Journal of Applied Bacteriology, 1990, pp. 739-749, vol. 69.
Margolles et al., Purification and Functional Characterization of a Novel µ- L-Arabinofuranosidase from *Bifidobacterium longum* B667, Applied and Environmental Microbiology, Sep. 2003, pp. 5096-5103, vol. 69, No. 9.
International Search Report issued in International Patent Application No. PCT/JP2011/057337, 4 pages.
Margolles et al., Purification and Functional Characterization of a Novel α-L-Arabinofuranosidase from *Bifidobacterium longum* B667, Applied and Environmental Microbiology, Sep. 2003, pp. 5096-5103, vol. 69, No. 9.
European Patent Office, Search Report issued in Application No. 11759569.4, mailed Sep. 6, 2013, 6 pp.
Roy, "Media for the isolation and enumeration of bifidobacteria in dairy products," International Journal of Food Microbiology, 69:167-182, 2001.

* cited by examiner

*Primary Examiner* — Blaine Lankford, Jr.
*Assistant Examiner* — Lauren K Van Buren
(74) *Attorney, Agent, or Firm* — Wood, Herron & Evans, LLP

(57) ABSTRACT

There are provided a method of identifying the *longum* species alone, such as *Bifidobacterium longum* subsp. *longum* alone, and measuring the viable cell count thereof, amongst the bacterial cells to be tested which include a microorganism belonging to the genus *Bifidobacterium* by using a culture medium that contains L-arabinose as a sole sugar source; and also a culture medium which is useful as a selective medium for the above measurement method and which is also easy to prepare.

4 Claims, No Drawings

MEASUREMENT METHOD FOR VIABLE CELL COUNT, AND CULTURE MEDIUM

TECHNICAL FIELD

The present invention relates to a measurement method for the viable cell count of the *longum* species alone, amongst the bacterial cells tested which include bifidobacteria, and also to a culture medium which is useful as a selective medium for the above measurement method.

Priority is claimed on Japanese Patent Application No. 2010-72368, filed Mar. 26, 2010, the content of which is incorporated herein by reference.

BACKGROUND ART

Bifidobacteria are widely known as one of the useful group of intestinal bacteria, and a multitude of publications exist relating to the physiological significance of this group of bacteria. For example, it has become clear that bifidobacteria produce organic acids such as lactic acid and acetic acid within the intestine, and also have effects in terms of suppressing the multiplication of harmful bacteria, producing vitamins, and activating immunity and the like.

For this reason, various preparations containing live bifidobacterial cells have been proposed in the past (Non-Patent Document 1). In addition, for the purpose of maintaining good health through the ingestion of bifidobacteria, various food products have been developed that contain bifidobacteria, such as fermented milk products including yogurts, sweets, drinks, and health foods. Furthermore, infants who are fed with breast milk during their infancy and early childhood tend to have superior levels of bifidobacteria, and therefore products such as powdered milk for infants or children containing bifidobacteria and/or lactic acid bacteria are also being developed in countries outside Japan. Currently, the *longum* species are mainly added as bifidobacterial species to food products in the world market, and there are also some products which use the *breve* species in combination (Non-Patent Document 2).

It is thought that individual display of the viable count for useful bacteria added in the products is beneficial for consumers in terms of providing as much information on the products as possible. In addition, with respect to the display of viable cell counts, the law has been established in Indonesia to display the viable cell count for each useful bacterial species added to the products.

Currently, as a method for determining the viable cell count for either one of the bacterial species in the products containing both bifidobacteria and lactic acid bacteria, a method to use a culture medium in which only bifidobacteria grow or a method to culture lactic acid bacteria alone through aerobic cultivation has already been established.

In addition, as a method for identifying the species of bifidobacteria in the products containing several species of bifidobacteria or lactic acid bacteria and also determining the viable cell count thereof, there is a method in which they are determined either from the morphology (i.e., color, shape, or the like) of colonies formed anaerobically or from the morphology of bacteria through Gram staining, by growing bacteria smeared on a culture medium that is prepared by adding sterile defibrinated blood to a BL agar medium (Non-Patent Document 3).

CITATION LIST

Non-Patent Documents

[Non-Patent Document 1] "Research on bifidobacteria", written and edited by Tomotari Mitsuoka, published by Japan Bifidus Foundation (1994), pages 266 to 267

[Non-Patent Document 2] "Research on bifidobacteria", written and edited by Tomotari Mitsuoka, published by Japan Bifidus Foundation (1994), pages 282 to 283

[Non-Patent Document 3] "Method for the enumeration of bifidobacteria in fermented milks and fermented milk drinks", published by the *Bifidobacterium* Testing Methods Review Committee of the Japanese Association of Fermented Milks and Fermented Milk Drinks, March 2000, pages 1 to 13.

Summary of Invention

Technical Problem

However, in those cases where the morphologies of colonies or the shapes of bacteria are similar, specialized knowledge is required to determine the bacterial species with the method as described in the above Non-Patent Document 3. For this reason, it is sometimes very difficult to determine the viable cell count for each species. In addition, there are many foreign countries where it is impossible to obtain sterile defibrinated blood. In those countries, it is impossible to prepare a BL agar medium containing blood, and thus the above method cannot be employed.

Currently, because there are products containing both the *longum* species and the *breve* species as described above, and also because some of the *longum* species and the *animalis* species (including the *lactis* species) exhibit similarities in the assimilation of sugars, a technique through a culture method has been required which can easily determine the viable cell count for the *longum* species alone in the products where the *longum* species and other species of bifidobacteria (such as the *breve* species and the *animalis* species) are both present.

The present invention aims to address the problems outlined above, and has an object of providing a measurement method capable of easily determining the viable cell count for the *longum* species alone, amongst the bacterial cells tested which include bifidobacteria, by using a specific culture method; and a culture medium which is useful as a selective medium for the above measurement method and which is also easy to prepare.

Solution to Problem

In order to solve the above problems, the inventors of the present invention have conducted detailed studies on the sugars and saccharides listed in Tables 15.51 and 15.54 in Bergey's Manual of Systematic Bacteriology (1986, vol. 2, page 1,428). As a result of intensive and extensive investigation, the inventors of the present invention discovered that, amongst the *longum* species, the *animalis* species, the *breve* species and the *infantis species*, two species (namely, the *longum* species and the *animalis* species) exhibit the assimilation mode for L-arabinose during the viable cell count through a culture method. Furthermore, the inventors of the present invention found that, amongst the *longum* species and the *animalis* species, only the *longum* species form large colonies when using a culture medium that contains L-arabinose at a specific concentration as a sole sugar source and also contains specific components at specific concentrations as media components other than sugars (such as proteins, peptides, and the like), thereby completing the present invention.

The measurement method and the culture medium according to the present invention that achieve the object described above include the following aspects.

[1] A method for measuring a viable cell count of a microorganism belonging to *Bifidobacterium longum* subsp. *longum*, amongst bacteria to be tested which include a microorganism belonging to the genus *Bifidobacterium*, through the use of a culture medium, the method characterized in that the aforementioned culture medium meets the following requirements 1) to 3), and the aforementioned viable cell count is determined by measuring the colonies having a diameter of 0.7 mm or larger which are formed in the aforementioned culture medium:

1) contains L-arabinose as a sole sugar source;
2) contains peptone, a meat extract and a yeast extract as nitrogen sources; and
3) contains no magnesium sulfate or manganese sulfate in the culture medium.

[2] The method according to the above aspect [1] in which a concentration of the aforementioned L-arabinose in the culture medium is 2 to 3% by mass, relative to the total mass of the culture medium.

[3] The method according to the above aspect [1] or [2] in which a content of the aforementioned peptone is 6.0 to 14.0 g/1,000 mL, a content of the aforementioned meat extract is 6.0 to 14.0 g/1,000 mL, and a content of the aforementioned yeast extract is 1.8 to 4.2 g/1,000 mL, in 1,000 mL of the culture medium.

[4] The method according to any one of the above aspects [1] to [3] in which the microorganism belonging to *Bifidobacterium longum* subsp. *longum* is a *Bifidobacterium longum* subsp. *longum* BB536 strain.

[5] The method according to any one of the above aspects [1] to [4] in which the aforementioned bacteria to be tested include, as the aforementioned microorganism belonging to the genus *Bifidobacterium*, the aforementioned microorganism belonging to *Bifidobacterium longum* subsp. *longum* and at least one type of microorganism selected from the group consisting of a microorganism belonging to *Bifidobacterium breve*, a microorganism belonging to *Bifidobacterium animalis* subsp. *lactis*, and a microorganism belonging to *Bifidobacterium longum* subsp. *infantis*.

[6] The method according to the above aspect [5] in which the aforementioned microorganism belonging to *Bifidobacterium breve* is a *Bifidobacterium breve* M-16V strain.

[7] A culture medium for measuring a viable cell count of a microorganism belonging to *Bifidobacterium longum* subsp. *longum* alone, amongst bacteria to be tested which include a microorganism belonging to the genus *Bifidobacterium*, which is used in the method described in any one of the above aspects [1] to [6].

[8] The culture medium according to the above aspect [7] containing: L-arabinose as a sole sugar source and in which a concentration of the aforementioned L-arabinose in the culture medium is 2 to 3% by mass, relative to the total mass of the culture medium; a yeast extract of 1.8 to 4.2 g/1,000 mL; a meat extract of 6.0 to 14.0 g/1,000 mL; and peptone of 6.0 to 14.0 g/1,000 mL, in 1,000 mL of the culture medium.

In the description and the claims of the present invention, concentration (%) values represent w/v (mass/volume) values.

In this description, "*bifidobacterium*" refers to a microorganism which belongs to the genus *Bifidobacterium*.

In addition, in this description, the *longum* species refers to a microorganism which belongs to *Bifidobacterium longum* subsp. *longum*, the *breve* species refers to a microorganism which belongs to *Bifidobacterium breve*, the *animalis* species refers to a microorganism which belongs to *Bifidobacterium animalis*, the *lactis* species refers to a microorganism which belongs to *Bifidobacterium animalis* subsp. *lactis* and the *infantis* species refers to a microorganism which belongs to *Bifidobacterium longum* subsp. *infantis*.

The term "bacteria powder" refers to bacteria that have been converted to a powdered form.

Advantageous Effects of Invention

According to the present invention, there are provided a measurement method capable of easily measuring the viable cell count of *longum* species alone, amongst the bacterial cells tested which include bifidobacteria, by using a specific culture method; and a culture medium which is useful as a selective medium for the above measurement method and which is also easy to prepare.

DESCRIPTION OF EMBODIMENTS

In the measurement method according to the present invention, the viable cell count of the *longum* species alone is determined, amongst the bacterial cells tested which include bifidobacteria, by using a culture medium that contains L-arabinose as a sole sugar source.

The culture medium will be described later in detail.

There are no particular limitations on the bacterial strain of *longum* species, and the bacterial strain may be a deposited strain from a public microorganism depository which has been deposited in the public culture collections (such as ATCC, NTCC, JCM, DSMZ, BCCM and LMG) to date as a strain belonging to the *longum* species, or may be a strain isolated from nature by known methods. Examples of the deposited strain from a public microorganism depository include the ATCC15707$^T$ strain and the BB536 strain (deposited under the Deposition Number: ATCC BAA-999 and commercially available from Morinaga Milk Industry Co., Ltd. as the BB536 bacteria powder). The superscript T denotes a type strain.

The bifidobacteria included in the bacteria to be tested may consist of the *longum* species alone. However, in view of the usefulness of the present invention, in addition to the *longum* species, it is preferable to include at least another type of bifidobacteria other than the *longum* species.

There are no particular limitations on the aforementioned another type of bifidobacteria other than the *longum* species, and examples thereof include bifidobacteria that are widely used in general as probiotic bacteria. Of these, it is preferable to include at least one type of species selected from the *breve* species, the *lactis* species and the *infantis* species, since the colonies they form on the aforementioned culture medium have small sizes and can be easily distinguished from the colonies formed by the *longum* species. Among them, it is preferable to include at least one type of strain selected from the ATCC 15700$^T$ strain (*breve* species), the M-16V strain (*breve* species) (deposited under the Deposition Number: BCCM/LMG23729), the DSM 10140$^T$ strain (*lactis* species) and the ATCC 15697$^T$ strain (*infantis* species), and it is particularly desirable to include the M-16V strain (*breve* species).

There are no particular restrictions on the types of samples containing bacteria to be tested which can be measured for viable cell count using the present invention, provided the sample contains bacteria to be tested. Specific examples thereof include various food products such as fermented milk products, sweets, drinks, health foods and powdered milk for infants or children, products such as drugs and livestock feed, and other products prepared by processing the above products through grinding, dilution with a diluent, or the like.

With respect to the incubation of the aforementioned sample, apart from the use of the culture medium according to the present invention as a culture medium, known culture methods which have been conventionally used to determine the viable cell count of microorganisms through culture methods can be employed. Examples of the aforementioned culture methods include a solid culture method (namely, a culture method in which culturing is performed on an agar medium).

Specific examples of the solid culture method include the pour plate method, the spread plate method and the spiral plate method. The pour plate method is a method in which a test sample (i.e., a sample or a diluted material prepared by diluting the sample with a diluent) is mixed with a heated and melted agar medium, and the mixture is then cooled, solidified and cultured. The spread plate method is a method in which a test sample is smeared across the top of an agar medium and then cultured. The spiral plate method is a method in which a test sample is plated on a culture medium with a concentration gradient using an instrument or the like.

More specifically, the measurement method according to the present invention can be carried out in the following manner. A test sample (i.e., a sample or a diluted material prepared by diluting the sample with a diluent) is cultured with the culture medium according to the present invention which contains agar to a concentration of about 1.5%, and the number of colonies with a predetermined size or larger (for example, those having a diameter of 0.7 mm or more) among the formed colonies is counted. The number of colonies counted at this time corresponds with the viable cell count of the *longum* species contained within the tested sample cultured on the aforementioned agar medium. Accordingly, the viable cell count (/g) for the *longum* species contained in the sample can be determined from this value and the dilution ratio.

There are no particular limitations on the diluent, and known diluents such as physiological saline and the diluent (A) described in the above-mentioned Non-Patent Document 3 (the anaerobic sample diluent disclosed in "Standard Methods of Analysis in Food Safety Regulation") can be used.

In terms of the culture conditions in the present invention, conventional culture conditions may be employed as a condition for culturing the *longum* species.

The number of colonies is usually counted through visual inspection after 48 hours of incubation at 37° C. under anaerobic conditions.

The culture medium used in the aforementioned measurement method according to the present invention contains L-arabinose as a sole sugar source.

In the culture medium, the concentration of L-arabinose is preferably 2 to 3% by mass, and more preferably 2 to 2.5% by mass, relative to the total mass of the culture medium.

It should be noted that examples of the sugar source other than the aforementioned L-arabinose that are not included in the culture medium of the present invention include glucose, starch, sucrose, raffinose, galactose, sorbitol and mannitol.

The aforementioned culture medium may contain a component other than L-arabinose. Hereafter, the components that constitute the aforementioned culture medium, other than L-arabinose serving as a sole sugar source, will be described as basal medium components.

Examples of the basal medium components include nitrogen sources such as yeast extract, meat extract and peptone; and other salts including sodium salts such as sodium chloride, sodium acetate and sodium propionate, L-cysteine hydrochlorides, phosphates and sulfates. Among these, the culture medium used in the measurement method of the present invention contains yeast extract, meat extract and peptone as nitrogen sources.

As the yeast extract, meat extract and peptone, each of those that are generally used for the cultivation of microorganisms can be used.

Yeast extract is a source of nutrition produced using yeasts as a raw material which is moderately broken down by autolytic enzymes, and specific examples thereof include the Yeast Extract product (manufactured by Becton, Dickinson and Company). Meat extract is a source of nutrition obtained from the meat exudate which complements the properties of peptone nutrition by providing essential elements such as minerals, phosphoric acid and energy sources that are absent in peptone. Specific examples thereof include the 'LAB-MEMCO' powder (manufactured by Oxoid Ltd.). Peptone is prepared by partial hydrolysis of milk casein, meat, soy protein or the like with a proteolytic enzyme or an acid. Specific examples thereof include Bacto™ peptone (manufactured by Becton, Dickinson and Company).

The content of yeast extract is preferably 1.8 to 4.2 g/1,000 mL, and more preferably 2.7 to 4.2 g/1,000 mL, in 1,000 mL of the culture medium.

The content of meat extract is preferably 6.0 to 14.0 g/1,000 mL, and more preferably 9.0 to 14.0 g/1,000 mL.

The content of peptone is preferably 6.0 to 14.0 g/1,000 mL, and more preferably 9.0 to 14.0 g/1,000 mL.

Each of the above contents of yeast extract, meat extract and peptone (g/1,000 mL) indicate the solid content (g) included in 1,000 mL of the culture medium.

From the viewpoint of osmotic pressure, the culture medium used in the present invention preferably contains the aforementioned salts. As the aforementioned salts, sodium salts are preferred, and sodium chloride and sodium acetate are particularly desirable.

The content of the aforementioned salts is preferably 5 to 15 g/1,000 mL, in 1,000 mL of the culture medium.

However, the culture medium used in the measurement method of the present invention does not contain magnesium sulfate or manganese sulfate. In other words, it is preferable that neither magnesium sulfate nor manganese sulfate is contained in order to grow the colonies of the *longum* species to an identifiable size (for example, equal to or more than 0.7 mm in diameter).

The culture medium according to the present invention may also include other components besides the above-mentioned components, if necessary, provided that these other components do not impair the effects of the present invention.

There are no particular limitations on these other components, and the types of components typically added to a culture medium may be used. For example, agar is added in those cases where the solid culture method is employed as a culture method in the measurement of the viable cell count. Agar is usually added so that the final concentration thereof achieved within the culture medium is about 1.5%.

Furthermore, any antibiotic can be added thereto, provided that the growth of colonies and the viable cell count of the *longum* species are not adversely affected.

By using a culture medium containing L-arabinose for which the *longum* species exhibit the mode of assimilation as a sole sugar source as described above, it is possible to identify the *longum* species alone and to easily measure the viable cell count thereof in the products where several types of bifidobacteria including the *longum* species coexist. In other words, only the *longum* species form large colonies in such a culture medium.

For example, even the colonies formed by the *animalis* species (*lactis* species) that exhibit similar mode of L-arabinose assimilation in the culture medium according to the present invention have smaller sizes than those formed by the *longum* species.

The size of the colonies becomes even smaller in the cases of bifidobacterial species (such as the *breve* species and *infantis* species) with no capacity for L-arabinose assimilation. It is thought that the reason for causing this difference in colony size is due to the aforementioned composition of the culture medium which reduces the colony forming capacity of the bifidobacterial species other than the *longum* species.

For this reason, when the products where several types of bifidobacteria including the *longum* species coexist are cultured using the culture medium of the present invention, it is possible to identify the *longum* species alone and to measure the viable cell count thereof by counting the number of colonies grown to a large size, which is simple and easy, without examining the shapes of colonies and bacteria. In addition, the measured values are about as accurate as those obtained with existing culture media, such as the aforementioned culture medium prepared by adding sterile defibrinated blood to the BL agar medium.

Therefore, the culture medium of the present invention is useful as a selective medium for measuring the viable cell count of *longum* species within the product where several types of bifidobacteria including the *longum* species coexist, through a culture method.

Moreover, it is also easy to prepare the culture medium according to the present invention since the materials that are difficult to obtain such as sterile defibrinated blood are not required.

In obtaining the above effects, it is important that each of the components serving as nitrogen sources (namely peptone, meat extract and yeast extract) is combined at predetermined concentrations.

Note that it is preferable that the culture medium according to the present invention contain no magnesium sulfate or manganese sulfate, in order to improve the colony growth.

There are no particular limitations on the method for preparing the culture medium, and the medium can be prepared using known methods.

More specifically, first, optional components such as agar, sodium chloride, sodium acetate and L-cysteine hydrochloride together with water are added and dissolved in the mixture of yeast extract, meat extract and peptone to prepare a basal medium. The concentrations of each component in the basal medium at this time point are adjusted to a level of about 1.25 times as high as the final concentrations thereof. Next, the above basal medium is sterilized for 15 minutes at 121° C. in an autoclave.

A sugar solution is prepared separately by dissolving a sugar (L-arabinose) in water. The concentration of sugar in the sugar solution at this time point is adjusted to a level of about 5 times as high as the final concentration thereof. Next, the sugar solution is sterilized by filter sterilization.

Then, the basal medium and the sugar solution are mixed at a ratio of 4:1 (volume ratio), thereby yielding a culture medium containing each component at a desired concentration. In this description of the present invention, 1,000 mL of the culture medium refers to a culture medium which is prepared by diluting the basal medium components and sugars with water to make up a total volume of 1,000 mL.

It should be noted that in the present invention, the culture medium used in the method for measuring the viable cell count of the *longum* species alone amongst the bacteria to be tested including bifidobacteria can also be described as a selective medium for the *longum* species, a selective medium for the *longum* species that contains L-arabinose as a sole sugar source, or the like.

EXAMPLES

A more detailed description of the present invention is presented below based on a series of test examples and examples, although the present invention is in no way limited by the following examples.

Test Example 1

Study on L-Arabinose Concentration

As a basal medium, 1.8 g of yeast extract (Yeast Extract, manufactured by Becton, Dickinson and Company), 6.0 g of meat extract ('LAB-LEMCO' powder, manufactured by Oxoid Ltd.), 6.0 g of peptone (Bacto peptone, manufactured by Becton, Dickinson and Company), 3.0 g of sodium chloride, 1.8 g of sodium acetate, 0.3 g of L-cysteine hydrochloride, and 15 g of agar were weighed, followed by the addition of water thereto, and the resulting mixture was used as a basal medium.

A sugar solution was prepared by dissolving L-arabinose in water so that the final concentration in the culture medium would be the sugar level as indicated in Table 1. Then, the basal medium and the sugar solution were mixed, thereby yielding culture media 1-1 to 1-4. In Table 1, the expression "%" denotes "% by mass".

The viable cell count through a culture method (pour plate method) was carried out by the following procedure using the prepared culture medium.

As the test sample, a BB536 bacteria powder (manufactured by Morinaga Milk Industry Co., Ltd., a product containing $1.2 \times 10^{11}$ cells/g) was used.

A 0.85% physiological saline solution was used as a diluent for diluting the test sample during the viable cell count.

The test sample (BB536 bacteria powder) was diluted with a diluent (0.85% physiological saline solution) to prepare a measurement sample.

The measurement sample was poured onto a plate through a pour plate method together with the culture medium (1-1 to 1-4), which was dissolved in advance by heating to 45° C. After forming the culture medium due to the solidification of agar, incubation at 37° C. under anaerobic conditions was performed for 48 hours. Following the incubation, the number of colonies that had grown on the culture medium was counted through visual inspection, and the number of viable bacterial cells within the test sample was calculated from this measured value.

The results are shown in Table 3. In addition, the diameters (mm) of the colonies were measured using a 0.1 mm scale, and the average value thereof was determined. The average value determined as described above is indicated in Table 3 as "colony diameter".

TABLE 1

| | Sugar | Sugar concentration | Viable cell count | Colony diameter (mm) |
|---|---|---|---|---|
| 1-1 | L-arabinose | 1.0% | $8.3 \times 10^{10}$ cells/g | 0.6 |
| 1-2 | L-arabinose | 1.5% | $1.2 \times 10^{11}$ cells/g | 0.6 |
| 1-3 | L-arabinose | 2.0% | $1.3 \times 10^{11}$ cells/g | 0.8 |
| 1-4 | L-arabinose | 3.0% | $1.0 \times 10^{11}$ cells/g | 0.9 |

As indicated in the results shown in Table 1, in the culture media 1-1 and 1-2 where the L-arabinose concentrations were from 1.0 to 1.5%, relative to the total mass of the culture medium, the size of the formed colonies was small, which made the measurement by visual observation relatively difficult. In the culture media 1-3 and 1-4 where the L-arabinose concentrations were from 2.0 to 3.0% by mass, relative to the total mass of the culture medium, colonies having a diameter of 0.8 to 0.9 mm were formed which were easily measured by visual observation, and the measured values for the number of viable bacterial cells were also close to the actual number of bacterial cells ($1.2 \times 10^{11}$ cells/g).

Test Example 2

Study on Basal Medium

The studies on the active ingredient concentrations in the basal medium were conducted through use of the media prepared by employing a basal medium A, B, B-1 or B-2 which contained each of the basal medium components listed in Table 2, and adjusting the concentrations (1.0-fold concentration) of each component in the respective basal media to concentrations indicated in Table 3. The concentration ratio indicated in Table 3 represents a ratio of change in the concentration of each basal medium component in 1,000 mL of the basal medium, based on the concentration of each basal medium component listed in Table 2 (set as 1.0-fold), while maintaining the mixing ratio listed in Table 2.

In general, the Reinforced Clostridial Medium Agar (RCA medium), the modified de Man Rogosa and Sharpe (mMRS) medium prepared by adding L-cysteine hydrochloride to the MRS medium, or the like is used for the determination of viable cell count of bifidobacteria. Accordingly, based on the medium compositions of RCA medium and mMRS medium, the basal media containing each basal medium component listed in Table 2 were prepared.

Agar was added to each of the above basal media so that the final concentration thereof (i.e., concentration following the addition of L-arabinose) was 1.5% by mass, relative to the total mass of the culture medium, and L-arabinose was further added thereto so that the final concentration thereof was 2% by mass, relative to the total mass of the culture medium, thereby preparing the respective culture media 2-1 to 2-11.

Measurement of the viable cell count through a culture method was carried out as in Test Example 1 using the obtained culture media.

The results are shown in Table 3.

TABLE 2

| Basal medium component | Basal medium | | | |
| --- | --- | --- | --- | --- |
| | A | B | B-1 | B-2 |
| Peptone | 10 | | | |
| Proteose peptone No. 3 | | 10 | 10 | 10 |
| Beef extract | 10 | 10 | 10 | 10 |
| Yeast extract | 3 | 5 | 5 | 5 |
| Polysorbate 80 | | 1 | | |
| Magnesium sulfate | | 0.1 | | 0.1 |
| Manganese sulfate | | 0.05 | | 0.05 |
| Ammonium citrate | | 2 | | |
| Sodium chloride | 5 | | | |
| Sodium acetate | 3 | 5 | 5 | 5 |
| L-cysteine hydrochloride | 0.5 | 0.5 | 0.5 | 0.5 |

Unit: g/1,000 mL

TABLE 3

| | Basal medium | | |
| --- | --- | --- | --- |
| | Type | Concentration (-fold) | Viable cell count | Colony diameter (mm) |
| 2-1 | Basal medium A | 0.6 | $9.9 \times 10^{10}$ cells/g | 0.9 |
| 2-2 | Basal medium A | 1.0 | $8.3 \times 10^{10}$ cells/g | 1.0 |
| 2-3 | Basal medium A | 1.2 | $8.1 \times 10^{10}$ cells/g | 0.9 |
| 2-4 | Basal medium A | 1.4 | $8.2 \times 10^{10}$ cells/g | 0.7 |
| 2-5 | Basal medium A | 1.6 | $<5.0 \times 10^{10}$ cells/g | — |
| 2-6 | Basal medium A | 1.8 | $<5.0 \times 10^{10}$ cells/g | — |
| 2-7 | Basal medium B | 0.3 | $7.5 \times 10^{10}$ cells/g | 0.4 |
| 2-8 | Basal medium B | 0.6 | $5.4 \times 10^{10}$ cells/g | 0.5 |
| 2-9 | Basal medium B | 1.0 | $5.7 \times 10^{10}$ cells/g | 0.6 |
| 2-10 | Basal medium B-1 | — | $7.7 \times 10^{10}$ cells/g | 0.9 |
| 2-11 | Basal medium B-2 | — | $7.9 \times 10^{10}$ cells/g | 0.6 |

As indicated in Table 3, amongst examples where the media having the same composition as that of the basal medium A were used, in the culture media 2-1 to 2-4 where the concentrations were 0.6 to 1.4-fold, colonies having a diameter of 0.7 mm or more were formed which were easily observed visually, and also the values for viable cell count remained stable from 8.1 to $9.9 \times 10^{10}$ cells/g.

On the other hand, in the culture media 2-5 to 2-6 where the concentrations were 1.6 to 1.8-fold, colonies were difficult to observe visually, and also the values for viable cell count were less than $5.0 \times 10^9$ cells/g, which were significantly lower than the actual number of bacterial cells. Accordingly, it was confirmed that the basal media in which the concentrations of each component constituting the basal medium A were within a range of 0.6 to 1.4-fold were effective as the basal media.

From these results, it was assessed that a basal medium containing 1.8 to 4.2 g of yeast extract, 6.0 to 14.0 g of meat extract and 6.0 to 14.0 g of peptone in a volume of 1,000 mL was effective as a basal medium in the present invention.

In addition, in the culture media 2-7 to 2-9 having the same composition as that of the basal medium B, the colonies formed had small diameters and were relatively difficult to measure visually, and also the values for viable cell count were not more than $7.5 \times 10^{10}$ cells/g.

Thus, it became clear that the composition of the basal medium B was unsuitable as a basal medium for the determination of viable cell count using the sugar assimilation modes.

In addition, in a basal medium B-1 prepared by removing polysorbate, magnesium sulfate, manganese sulfate, ammonium citrate and L-cysteine hydrochloride from the basal medium B, the colony diameter was 0.9 mm. On the other hand, the colony diameter was 0.6 mm in a basal medium B-2 prepared by adding magnesium sulfate and manganese sulfate to the basal medium B-1.

From these observations, it was considered that the absence of magnesium sulfate and manganese sulfate was the primary factor for the *longum* species to grow so that the colony diameter reached an identifiable size.

From these results, it was indicated, not that the viable cell count for the *longum* species can be carried out easily and accurately by simply replacing the sugar source in a culture medium of known composition with L-arabinose, but rather, it is essential that each component (namely, peptone, meat extract and yeast extract) is combined as nitrogen sources at predetermined concentrations, and it is also effective not to add magnesium sulfate and manganese sulfate.

Test Example 3

Study on Isolation Characteristics Due to Differences in Bifidobacteria Species

As bifidobacteria, the ATCC 15700$^T$ strain (*breve* species), the M-16V strain (*breve* species), the ATCC 15707$^T$ strain (*longum* species), the BB536 strain (*longum* species) and the DSM 10140$^T$ strain (*lactis* species) were used. The superscript T indicates a type strain.

Of the above strains, the M-16V strain (*breve* species) is deposited under the Deposition Number: BCCM/LMG23729, and the BB536 strain (*longum* species) is deposited under the Deposition Number: ATCC BAA-999.

The assimilation modes of *breve* species, *infantis* species, *longum* species and *lactis* species for L-arabinose are shown in Table 4.

TABLE 4

| Bacterial species | L-arabinose |
|---|---|
| *Breve* species | − |
| *Infantis* species | − |
| *Longum* species | + |
| *Lactis* species (described as *Animalis* species) | + |

+: 90% or more bacterial strains exhibited assimilation mode
−: 90% or more bacterial strains exhibited no assimilation mode
(Excerpt from Bergey's Manual of Systematic Bacteriology, vol. 2, page 1,428, Table 15.51)

preparing the respective culture media 3-1 to 3-14. In this process, D-glucose was added so that the final concentration thereof was 1% by mass, and L-arabinose was added so that the final concentration thereof was 2% by mass, relative to the total mass of the culture medium.

Each of the above strains was subcultured at 37° C. for 15 hours in the mMRS culture solution by transferring the originally grown culture thereto in an amount of 3%. The culture solution in which the stable growth was confirmed was diluted with 0.85% physiological saline to an appropriate concentration.

The diluted culture solution was poured onto a plate through a pour plate method together with the culture medium (3-1 to 3-14), which was heated to 45° C. and dissolved in advance. After the solidification of agar, incubation at 37° C. under anaerobic conditions was performed for 48±2 hours. Following the incubation, the diameters (mm) of the colonies that had grown on the culture medium were measured as in Test Example 1. The results are shown in Table 5.

In Table 5, the expression "N. T." indicates that no test (namely, incubation and measurement of colony diameters) has been carried out. Further, in Table 5, the expression "%" denotes "% by mass".

TABLE 5

| | | 3-1 | 3-2 | 3-3 | 3-4 | 3-5 | 3-6 | 3-7 |
|---|---|---|---|---|---|---|---|---|
| | | No added sugars | | | | 1% D-glucose | | |
| Bacterial species | Bacterial strains | 0.3-fold | 0.6-fold | 0.9-fold | 1.0-fold | 0.3-fold | 0.6-fold | 0.9-fold |
| *Breve* species | ATCC 15700$^T$ | 0.2 | 0.2 | 0.3 | 0.2 | 1.2 | 1.4 | 1.6 |
| *Breve* species | M-16V | <0.2 | 0.2 | 0.2 | 0.2 | 0.7 | 1.0 | 1.0 |
| *Infantis* species | ATCC 15697$^T$ | 0.2 | 0.2 | 0.3 | 0.3 | 1.2 | 1.3 | 1.4 |
| *Longum* species | ATCC 15707$^T$ | <0.2 | <0.2 | 0.2 | <0.2 | 0.8 | 1.3 | 1.7 |
| *Longum* species | BB536 | <0.2 | <0.2 | 0.2 | <0.2 | 0.6 | 1.0 | 1.5 |
| *Lactis* species | DSM 10140$^T$ | <0.2 | 0.2 | 0.3 | 0.3 | 0.4 | 0.7 | 1.0 |
| | | 3-8 | 3-9 | 3-10 | 3-11 | 3-12 | 3-13 | 3-14 |
| | | | | 2% L-arabinose | | | | |
| Bacterial species | Bacterial strains | 0.1-fold | 0.3-fold | 0.45-fold | 0.6-fold | 0.75-fold | 0.9-fold | 1.0-fold |
| *Breve* species | ATCC 15700$^T$ | N.T | 0.2 | N.T | 0.2 | N.T | 0.3 | 0.2 |
| *Breve* species | M-16V | N.T | 0.2 | N.T | 0.2 | N.T | 0.2 | <0.2 |
| *Infantis* species | ATCC 15697$^T$ | N.T | 0.2 | N.T | 0.3 | N.T | 0.3 | 0.3 |
| *Longum* species | ATCC 15707$^T$ | 0.3 | 0.7 | 1.0 | 1.0 | 1.5 | 1.4 | 1.6 |
| *Longum* species | BB536 | N.T | 0.5 | 0.8 | 1.1 | 1.0 | 1.2 | 1.0 |
| *Lactis* species | DSM 10140$^T$ | N.T | 0.3 | 0.4 | 0.6 | 0.4 | 0.5 | 0.3 |

A culture medium containing the aforementioned basal medium A (i.e., 3 g of yeast extract, 10 g of meat extract, 10 g of peptone, 5 g of sodium chloride, 3 g of sodium acetate and 0.5 g of L-cysteine hydrochloride) in a volume of 1,000 mL, and basal media in which the aforementioned basal medium A (having a 1.0-fold concentration) was diluted so that the concentrations of each component of the basal medium A were adjusted to those shown in Table 5 (0.1 to 0.9-fold) were prepared.

Agar was added to each of the above basal media so that the final concentration thereof (i.e., concentration following the addition of L-arabinose) was 1.5% by mass, relative to the total mass of the culture medium, and D-glucose or L-arabinose was further added thereto as a sugar source, thereby As indicated in the results shown in Table 5, in those cases where the culture media (3-1 to 3-4) with no added sugar were used, only colonies not larger than 0.3 mm in diameter grew, regardless of the bacterial strains tested.

In those cases where the culture media (3-5 to 3-7) to which 1% by mass of D-glucose was added were used, the diameter of the formed colonies increased proportional to the concentrations of the components of culture media. In the culture media where the concentrations of the medium components were 0.6-fold or higher, colonies equal to or larger than 0.7 mm in diameter were formed, regardless of the bacterial species, although no difference was observed among the bacterial species.

In those cases where the culture media (3-8 to 3-14) to which 2% by mass of L-arabinose was added were used, both two strains of longum species formed colonies that were equal to or larger than 0.8 mm in diameter when the concentrations of the medium components were 0.45-fold or higher. On the other hand, other bacterial species were only capable of forming small colonies. For example, even the DSM 10140$^T$ strain (lactis species) exhibiting the assimilation mode for L-arabinose was only capable of forming colonies up to 0.6 mm in diameter while other bacterial strains could only form colonies that are not larger than 0.3 mm.

From these results, it was shown that by using a culture medium in which a predetermined amount of L-arabinose was added to a specific basal medium, it was possible to identify the *longum* species alone and to easily measure the viable cell count thereof even if other bifidobacterial species exhibiting the assimilation mode for L-arabinose such as the *lactis* species were also present.

In other words, it was shown that by using the above culture medium, it is possible to increase the size of the colonies formed only by the *longum* species, and to easily determine the viable cell count thereof.

Text Example 4

Measurement of the viable cell count through a culture method was carried out as in Test Example 1 using the culture solution of the ATCC 15707$^T$ strain (longum species) prepared in Test Example 3 as the test sample and using the culture media 3-8 to 3-14 prepared in Test Example 3 and the RCA medium as the culture media. The results are shown in Table 6. In Table 6, the expression "%" denotes "% by mass".

TABLE 6

*Longum* sp. ATCC 15707$^T$ strain

| | Concentration of basal medium component (-fold) | Sugar | Viable cell count |
|---|---|---|---|
| 3-8 | 0.1 | 2% L-arabinose | $1.5 \times 10^9$ cells/mL |
| 3-9 | 0.3 | 2% L-arabinose | $1.7 \times 10^9$ cells/mL |
| 3-10 | 0.45 | 2% L-arabinose | $1.6 \times 10^9$ cells/mL |
| 3-11 | 0.6 | 2% L-arabinose | $1.6 \times 10^9$ cells/mL |
| 3-12 | 0.75 | 2% L-arabinose | $1.7 \times 10^9$ cells/mL |
| 3-13 | 0.9 | 2% L-arabinose | $1.7 \times 10^9$ cells/mL |
| 3-14 | 1.0 | 2% L-arabinose | $1.8 \times 10^9$ cells/mL |
| RCA medium | | 0.5% D-glucose 0.1% soluble starch | $1.5 \times 10^9$ cells/mL |

As indicated in the results shown in Table 6, the viable cell count measured in the culture grown with the culture medium 3-8 in which the concentrations of basal medium components were 0.1-fold was equivalent to the viable cell count measured in the culture grown with the RCA medium. This concentration of 0.1-fold for the basal medium components is lower than the lower limit of 0.6 to 1.4-fold concentrations for the basal medium components, which are the required concentrations derived from the results of Test Example 2.

Therefore, it was demonstrated that it was possible to determine the viable cell count of *longum* species, as accurately as through the use of a conventional culture medium, by using a culture medium containing nitrogen sources (such as proteins and peptides) at 0.6 to 1.4-fold concentrations of the basal medium component A shown in Table 2; i.e., a culture medium in which a specific amount of L-arabinose was added to a basal medium containing 1.8 to 4.2 g of yeast extract, 6.0 to 14.0 g of meat extract and 6.0 to 14.0 g of peptone in a volume of 1,000 mL.

Example 1, Comparative Examples 1 and 2

A milk powder product known to contain both the bacteria powder of *longum* sp. BB 536 strain and the bacteria powder of *breve* sp. M-16V strain was prepared.

The viable cell count for each bacterial species within the aforementioned milk powder product was determined in the same manner as in Test Example 1 using three types of culture media; i.e., a BL agar medium containing sterile defibrinated horse blood (a conventional culture medium on which colonies were regarded as distinguishable from the shape thereof), the RCA medium (a culture medium on which both two strains of bifidobacteria were known to form colonies), and a culture medium prepared by adding L-arabinose to the following basal medium to a concentration of 2% (namely, the culture medium of the present invention). However, the incubation was carried out, only with the BL agar medium, by the spread method not the pour plate method.

Basal medium: a basal medium containing 2.5 g of yeast extract, 8.2 g of meat extract, 8.2 g of peptone, 4.1 g of sodium chloride, 4.1 g of sodium acetate, 0.41 g of L-cysteine hydrochloride and 15 g of agar in a volume of 1,000 mL.

In an example where the BL medium was used, the *longum* species and the *breve* species were counted separately based on the shape and microscopic visualization of the colonies grown on the BL medium. The combined total of these values are shown as the viable cell count for two species put together.

In the examples where the RCA medium and the culture medium of the present invention were used, the viable cell count was determined from the number of colonies obtained by growth.

In addition, in Table 7, the symbol "-" indicates that no count was made since the size of the colonies was less than 0.2 mm. Further, in Table 7, the expression "%" denotes "% by weight mass".

TABLE 7

| | Ex. 1 | Comp. Ex. 1 | Comp. Ex. 2 |
|---|---|---|---|
| Culture medium | Culture medium of the present invention | BL medium (spread method) | RCA medium |
| Sugar | 2% L-arabinose | 1% D-glucose | 0.5% D-glucose 0.1% soluble starch |
| *Longum* species | $1.5 \times 10^7$ cells/g | $1.5 \times 10^7$ cells/g | — |
| *Breve* species | — | $6.7 \times 10^6$ cells/g | — |
| Two species in total | — | $2.2 \times 10^7$ cells/g | $2.3 \times 10^7$ cells/g |

As indicated in the results shown in Table 7, the viable cell count measured using the culture medium of the present invention was equivalent to the viable cell count of *longum* species measured using the BL medium containing sterile defibrinated horse blood. Therefore, it was demonstrated that it was possible to identify *longum* species alone and to determine the viable cell count thereof by using the culture medium of the present invention, and the obtained viable cell count was also almost as accurate as the value when the aforementioned BL medium was used.

On the other hand, the viable cell count measured using the RCA medium was equivalent to the viable cell count of *longum* species and *breve* species put together measured using the BL medium containing sterile defibrinated horse blood.

Accordingly, when the RCA medium was used, it was impossible to distinguish the viable cell count of *longum* species from that of *breve* species.

INDUSTRIAL APPLICABILITY

According to the present invention, there are provided a measurement method capable of easily measuring the viable cell count of *longum* species alone, amongst the bacterial cells tested which include bifidobacteria, by using a specific culture method; and a culture medium which is useful as a selective medium for the above measurement method and which is also easy to prepare.

The invention claimed is:

1. A method for distinguishing *Bifidobacterium longum* subsp. *longum* from at least one of *Bifidobacterium breve*, *Bifidobacterium animalis* subsp. *lactis*, and *Bifidobacterium longum* subsp. *infantis* comprising: culturing microorganisms that include *Bifidobacterium longum* subsp. *longum* and at least one other microorganism selected from the group consisting of *Bifidobacterium breve*, *Bifidobacterium animalis* subsp. *lactis*, and *Bifidobacterium longum* subsp. *infantis* on a culture medium agar for at least 48 hours at a temperature of 37° C. under anaerobic conditions, measuring colonies produced, and only counting colonies having a diameter of 0.7 mm or larger to generate a cell count for *Bifidobacterium longum* subsp. *longum*, wherein said culture medium agar is free of magnesium sulfate and manganese sulfate and comprises L-arabinose as a sole sugar source with a concentration of 2 to 3% by mass, relative to the total mass of the culture medium agar, 6.0 to 14.0 g/1,000 mL of peptone, 6.0 to 14.0 g/1,000 mL of a meat extract, and 1.8 to 4.2 g/1,000 mL of a yeast extract.

2. The method according to claim 1, wherein said microorganism belonging to *Bifidobacterium longum* subsp. *longum* is a *Bifidobacterium longum* subsp. *longum* BB536 strain.

3. The method according to claim 1, wherein said microorganism belonging to *Bifidobacterium breve* is a *Bifidobacterium breve* M-16V strain.

4. A culture medium agar for distinguishing *Bifidobacterium longum* subsp. *longum* from at least one of *Bifidobacterium breve*, *Bifidobacterium animalis* subsp. *lactis*, and *Bifidobacterium longum* subsp. *infantis* comprising: a selective culture medium free of magnesium sulfate or manganese sulfate which is able to distinguish *Bifidobacterium longum* subsp. *longum* from at least one of *Bifidobacterium breve*, *Bifidobacterium animalis* subsp. *lactis*, and *Bifidobacterium longum* subsp. *infantis* containing L-arabinose as a sole sugar source with a concentration of 2 to 3% by mass, relative to the total mass of the culture medium agar, 6.0 to 14.0 g/1,000 mL of peptone, 6.0 to 14.0 g/1,000 mL of a meat extract, 1.8 to 4.2 g/1,000 mL of a yeast extract, wherein only *Bifidobacterium longum* subsp. *longum* is able to form colonies that are 0.7 mm or larger after an incubation of at least 48 hours at a temperature of 37° C. under anaerobic conditions.

* * * * *